(12) United States Patent
Tappura et al.

(10) Patent No.: US 10,018,563 B2
(45) Date of Patent: Jul. 10, 2018

(54) SAMPLE PLATE AND ANALYZING METHOD

(71) Applicant: Teknologian Tutkimuskeskus VTT OY, Espoo (FI)

(72) Inventors: Kirsi Tappura, Tampere (FI); Hannu Välimäki, Tampere (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 33 days.

(21) Appl. No.: 14/770,833

(22) PCT Filed: Feb. 27, 2014

(86) PCT No.: PCT/FI2014/050146
§ 371 (c)(1),
(2) Date: Aug. 27, 2015

(87) PCT Pub. No.: WO2014/131947
PCT Pub. Date: Sep. 4, 2014

(65) Prior Publication Data
US 2016/0011112 A1 Jan. 14, 2016

(30) Foreign Application Priority Data
Feb. 27, 2013 (FI) ...................................... 20135183

(51) Int. Cl.
*G01N 21/64* (2006.01)
*B01L 3/00* (2006.01)
(Continued)

(52) U.S. Cl.
CPC .......... *G01N 21/648* (2013.01); *B01L 3/5027* (2013.01); *G01N 21/6428* (2013.01);
(Continued)

(58) Field of Classification Search
None
See application file for complete search history.

(56) References Cited

U.S. PATENT DOCUMENTS 6,192,168 B1 * 2/2001 Feldstein ............. G01N 21/552
385/12
6,312,961 B1 11/2001 Voirin et al.
(Continued)

FOREIGN PATENT DOCUMENTS

FR 2783919 A1 3/2000
WO WO 0184197 A1 11/2001
(Continued)

OTHER PUBLICATIONS

Burghardt T P et al: Around-the-objective total internal reflection fluorescence microscopy. Oct. 11, 2009.
(Continued)

*Primary Examiner* — Betty J Forman
(74) *Attorney, Agent, or Firm* — Seppo Laine Oy

(57) ABSTRACT

A sample plate (1) and an analyzing method, wherein the sample plate (1) comprises a substrate (2), at least one sensor site (5) on a first surface (3) of the substrate (2) and at least one optical element (6) on a second surface (4) of the substrate (2). The sample plate (1) is further provided with a waveguide (7) on the second surface (4) for guiding an excitation signal to interact with the at least one sensor site (5). The method comprises bringing the sample in contact with at least one sensor site (5), exciting the sensor site (5) in order to obtain an emitted signal, and selectively collecting the emitted signal by means of at least one optical element (6) and utilizing a supercritical angle fluorescence method; and detecting the collected emitted signals by a detector. In the method, the sensor site (5) is excited by (Continued)

means of an evanescent field generated by the excitation signal propagating in a waveguide (7).

10 Claims, 2 Drawing Sheets

(51) Int. Cl.
  *G01N 21/77* (2006.01)
  *G01N 21/03* (2006.01)
  *G01N 21/05* (2006.01)
(52) U.S. Cl.
  CPC ..... *G01N 21/6452* (2013.01); *G01N 21/7703* (2013.01); *G01N 21/0303* (2013.01); *G01N 21/05* (2013.01); *G01N 2021/6439* (2013.01); *G01N 2021/6482* (2013.01)

(56) References Cited

U.S. PATENT DOCUMENTS

| | | |
|---|---|---|
| 6,714,297 B1 | 3/2004 | Ruckstuhl et al. |
| 2005/0048599 A1 | 3/2005 | Goldberg |
| 2005/0195394 A1 | 9/2005 | Ma et al. |
| 2006/0011862 A1 | 1/2006 | Berstein |
| 2006/0160209 A1 | 7/2006 | Larson et al. |
| 2009/0069199 A1 | 3/2009 | Brandenburg |
| 2009/0165876 A1* | 7/2009 | Atkin ................ B01L 3/502723 137/825 |
| 2010/0055666 A1* | 3/2010 | Wimberger-Friedl ..................... G01N 21/6454 435/4 |
| 2010/0320363 A1* | 12/2010 | Schleipen ............ G01N 21/645 250/200 |

FOREIGN PATENT DOCUMENTS

| | | |
|---|---|---|
| WO | WO2007108752 A1 | 9/2007 |
| WO | WO 2010035204 A1 | 4/2010 |
| WO | WO 2011141530 A2 | 11/2011 |
| WO | WO2012031234 A2 | 3/2012 |

OTHER PUBLICATIONS

Kyoung Je Cha et al: A portable pressure pump for microfluidic lab-on-a-chip systems using a porous polydimethylsiloxane sponge. Jun. 23, 2011.

* cited by examiner

SAMPLE PLATE AND ANALYZING METHOD

TECHNICAL FIELD

The present invention relates to sample plates and methods of analysing samples.

In particular, the present invention relates to sample plates and methods utilizing luminescence originating from sensor sites on the sample plates.

BACKGROUND ART

U.S. Pat. No. 4,810,658 discloses photometric instruments, their use in methods of optical analysis, and ancillary devices therefor. The method comprises optically analysing a test sample which comprises a sample material with light-absorbing, scattering, fluorescent, phosphorescent or luminescent properties. The sample is partly in a liquid phase and partly bound to an adjacent solid surface. The method comprises providing as said solid surface a surface of a transparent solid optical waveguide, and measuring light from the sample material bound to said solid surface that has passed into and through said transparent solid optical waveguide with total internal reflections and emerged from said waveguide at an angle that deviates from the optical axis of said waveguide.

U.S. Pat. No. 7,750,316 B2 discloses a polymer biochip for detecting fluorescence. The provided optical chip has one or more parabolic optical elements that capture and collimate the fluorescent light and direct it onto a detector. The optical chip may be constructed of a polymer and made using injection molding techniques.

US 2010/0243914 A1 discloses a scanning system that provides for detection based on supercritical angle fluorescence (SAF). The system provides for the optical coupling of a sample to the scanner in a sandwich structure that uses first and second refractive index matching materials to provide optical coupling through the sandwich arrangement.

WO 2011/141530 A2 discloses a sensor comprising a substrate having a first surface and a second surface. The first surface has at least one sensor site provided thereon. The substrate is configured such that on excitation of a sample provided at the sensor site, luminescence originating from the sensor site propagates into the substrate, the second surface of the substrate being configured to selectively transmit the luminescence propagating within the substrates at angles greater than the critical angle out of the substrate where it may be detected by a detector provided below the substrate. A specific type of luminescence mentioned in the WO publication is fluorescence, and more specifically supercritical angle fluorescence (SAF).

DISCLOSURE OF INVENTION

It is an object of the present invention to create a more convenient sample plate and analysing method.

According to an aspect of the invention, the sample plate comprises a substrate, at least one sensor site on a first surface of the substrate and at least one optical element on a second surface of the substrate. The sample plate is further provided with a waveguide on the second surface for guiding an excitation signal to interact with the at least one sensor site.

According to another aspect of the invention, the sample plate comprises a substrate and at least one sensor site on a first surface of the substrate. Additionally, the sample plate comprises a waveguide provided on a second surface of the substrate for guiding an excitation signal to generate an evanescent field for exciting the at least one sensor site, The sample plate further comprises at least one optical element provided on the second surface 4) for selectively collecting signals emitted in response to said excitation of the at least one sensor site.

According to an aspect of the invention, the method comprises bringing the sample in contact with at least one sensor site, exciting the sensor site in order to obtain an emitted signal, and selectively collecting the emitted signal by means of at least one optical element and utilizing a supercritical angle fluorescence method, and detecting the collected emitted signals by a detector. In the method, the sensor site is excited by means of an evanescent field generated by the excitation signal propagating in a waveguide.

The invention allows several embodiments with associated benefits and thus creates a more convenient sample plate and analysing method.

BRIEF DESCRIPTION OF DRAWINGS

For a more complete understanding of the present invention and the advantages thereof, the invention is now described with the aid of the embodiments and examples and with reference to the following drawings, in which.

MODES FOR CARRYING OUT THE INVENTION

Figure 1:
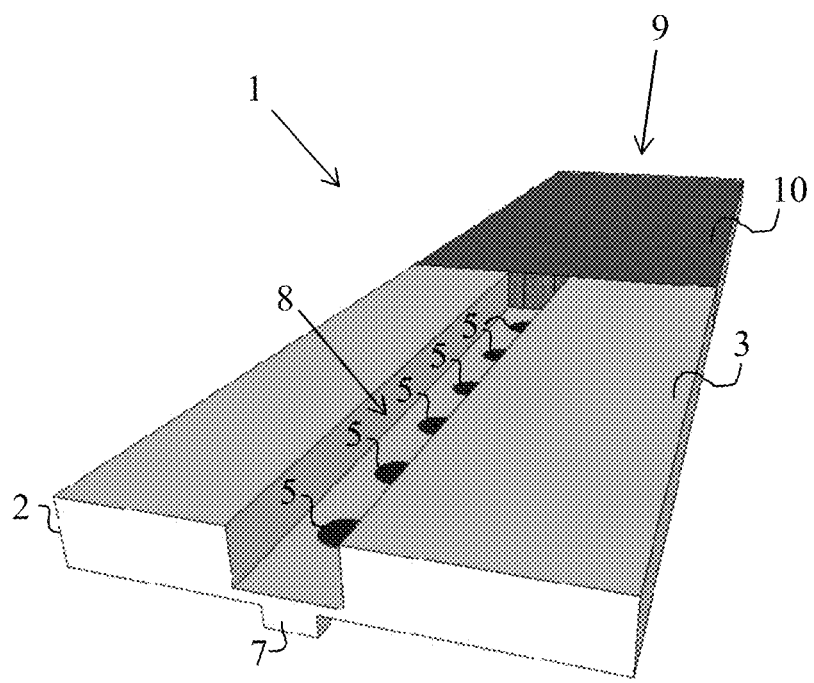
FIG. 1 presents a sample plate according to an embodiment.

FIG. 1 presents a sample plate 1 according to an embodiment. The sample plate 1 comprises a substrate 2, a first surface 3 of which is visible in FIG. 1. FIG. 1 shows also a fluid channel 8 formed by a longitudinal recess in the first surface 3 of the substrate 2. The sample plate 1 also comprises sensor sites 5 located at the bottom of the fluid channel 8. FIG. 1 shows also a second end of a waveguide 7 disposed on a second surface of the sample plate 1. FIG. 1 presents also a sample collection area 9 at a first end of the sample plate 1 and a resilient absorbent material 10 provided at the sample collection area 9. As shown in FIG. 1, a first end of the fluid channel 8 is connected to the resilient absorbent material 10 of the sample collection area 9 in order to allow a sample fluid to flow from the sample collection area 9 into the fluid channel 8. The sensor sites 5 are disposed along the fluid channel 8 so that the sample fluid flowing in the fluid channel 8 is brought into contact with the sensor sites 5.

Figure 2:
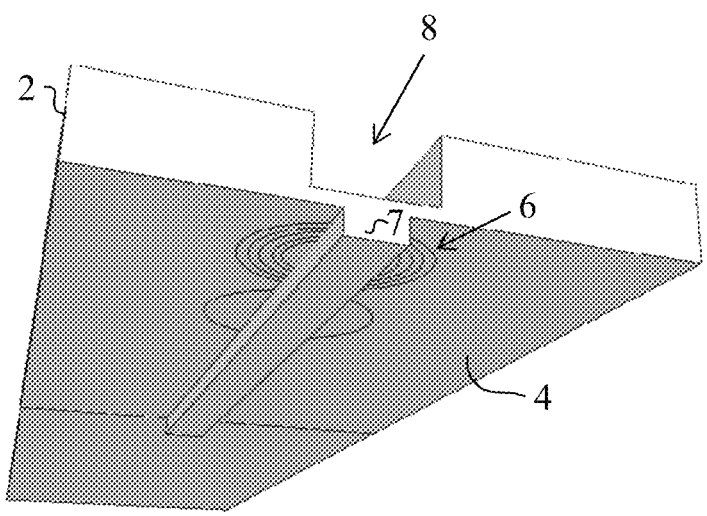
FIG. 2 presents the sample plate of FIG. 2 from a different direction.

FIG. 2 presents the sample plate of FIG. 2 from a different direction such that the second surface 4 of the substrate 2 is visible. FIG. 2 shows that the waveguide 7 is co-directional with the fluid channel 8 and extend substantially along the whole length of the fluid channel 8 on the opposite surface (second surface 4) of the substrate 2. The waveguide 7 is also located opposite to the bottom of the fluid channel 8 so that there is also a thin portion of the substrate 2 material between the sensor sites 5 and the waveguide 7. As shown in FIG. 2, the sample plate also comprises optical elements 6 disposed between the sensor sites 5 and the waveguide 7 in the vertical direction of the substrate 2. Herein, the vertical direction refers to the thickness direction of substrate 2, which is perpendicular to the planes generally defined by the first surface 3 and the second surface 4. Such optical elements 6 can be formed in the substrate 2 material, for instance. Alternatively, the optical elements 6 can be located "lower" in the vertical direction such that they are at least partially on the level of the waveguide 7 or "higher" such that they are at least partially on the level of the sensor sites 5.

In the lateral direction, which is co-directional with the planes generally defined by the first surface 3 and the second surface 4, the optical elements 6 are located around the sensor sites 5. This means that projections of the optical elements 6 on a plane generally defined by the first surface 3 and the second surface 4 at least partially surround the projections of the sensor sites 5 on such a plane.

Figure 3:
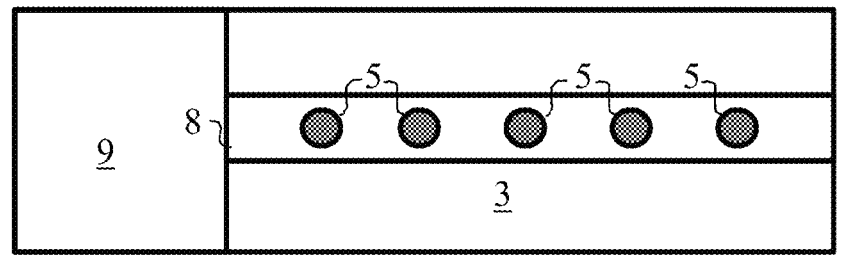
FIG. 3 presents a top view of a sample plate according to a second embodiment.

FIG. 3 presents a top view of a sample plate according to a second embodiment. The embodiment of FIG. 3 comprises elements equivalent to those shown in FIG. 1 and FIG. 2. FIG. 3 shows that a plurality of sensor sites 5 are disposed along the fluid channel 8 and spaced apart from each other.

Figure 4:
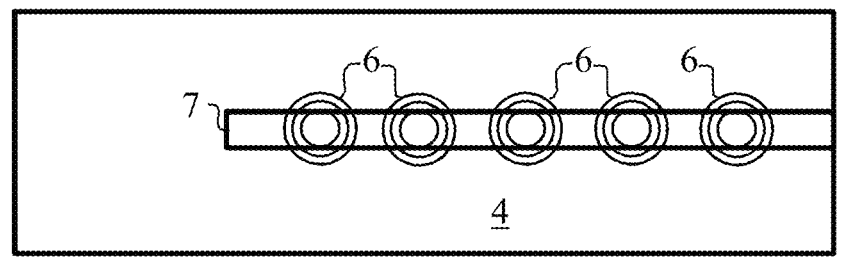
FIG. 4 presents a bottom view of the sample plate of FIG. 3.

FIG. 4 presents a bottom view of the sample plate of FIG. 3. FIG. 3 shows that a plurality of optical elements 6 are disposed along the waveguide and spaced apart from each other. Thus, the arrangement of the optical elements 6 corresponds to that of the sensor sites 5.

Figure 5:
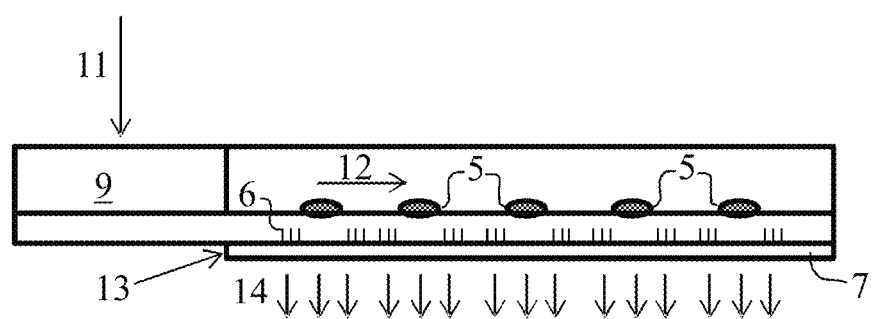
FIG. 5 presents a cross sectional side view of the sample plate of FIG. 3.

FIG. 5 presents a cross sectional side view of the sample plate of FIG. 3 (the dimensions shown are not to scale). FIG. 5 shows that the optical elements 6 are co-located with the sensor sites 5 but on the opposite surface of the substrate material.

FIG. 5 shows also arrows 11, 12, 13 and 14 intended to clarify the operation of the sample plate. The sample to be analyzed is loaded onto the sample collection area 9 as indicated by arrow 11. When the resilient absorbent material 10 of the sample collection area 9 is compressed or squeezed, the absorbed sample flows into the fluid channel 8 as indicated by arrow 12. Then, light is conducted into the waveguide 7 at its first end as indicated by arrow 13. The light propagated in the waveguide 7 and interacts with the luminescent molecules, such as fluorescent molecules, at the sensor sites 5. The molecules are thus excited to emit light, which is collected by the optical elements 6 and directed outside the sample plate as indicated by arrows 14. This light is then detected by a detector.

According to an embodiment, there is provided a sample plate 1 comprising a substrate 2 having a first surface 3 and a second surface 4. The first surface 3 and the second surface 4 are on the opposite sides of the sample plate 1. The sample plate 1 further comprises at least one sensor site 5 on the first surface 3 and at least one optical element 6 on the second surface 4. The sample plate 1 is provided with a waveguide 7 on the second surface 4 for guiding an excitation signal to interact with the at least one sensor site 5.

In this document, the excitation of the sensor site 5 means the excitation of the relevant molecules within or at the sensor site 5 or on the sensor site 5 or forming the sensor site 5.

According to another embodiment, the sample plate 1 is configured such that the excitation signal propagating in the waveguide 7 by total internal reflections generates an evanescent field interacting with the at least one sensor site 5.

According to a further embodiment, the sample plate 1 is configured such that, on excitation of a sample provided at the at least one sensor site 5, fluorescent light originating from the sensor site 5 propagates into the substrate 2. Further, the at least one optical element 6 selectively transmits the fluorescent light within the substrate 2 at angles greater than the critical angle out of the substrate 2 for detection by a detector.

According to a further embodiment, the sample plate comprises a fluid channel 8 defined by a recess in the first surface and the at least one sensor site 5 is located within the fluid channel 8.

According to a further embodiment, the sample plate comprises a sample collection area 9 connected to the fluid channel 8. In this embodiment, the sample plate 1 is configured to receive a fluid sample at the sample collection area 9 and transport at least a portion of the fluid sample via the fluid channel 8 to the at least one sensor site 5.

According to a further embodiment, the sample plate comprises resilient absorbent material 10 at the sample collection area 9. This resilient absorbent material 10 is configured to absorb the fluid sample and release at least a portion of the absorbed the fluid sample to the fluid channel 8 when the resilient absorbent material 10 is pressed.

According to a further embodiment, the waveguide 7 is co-directional with the fluid channel 8.

According to a further embodiment, the at least one sensor site 5 comprises a plurality of sensor sites 5 located along the fluid channel 8.

According to a further embodiment, the at least one optical element 6 comprises an individual optical element 6 disposed in a vertical direction between the waveguide 7 and each individual sensor site 5.

According to a further embodiment, the at least one optical element 6 comprises an individual optical element 6 for each individual sensor site 5 disposed such that the optical element 6 at least partially surrounds a portion of the material of the substrate 2 between the waveguide 7 and the respective sensor site 5. According to a further embodiment, the at least one optical element 6 comprises an individual optical element 6 disposed in a vertical direction at least partially at the level of the waveguide 7.

According to a further embodiment, the at least one optical element 6 comprises an individual optical element 6 disposed in a vertical direction between the waveguide 7 and each individual sensor site 5 and in a lateral direction such that it at least partially surrounds a portion of the material of the substrate 2 between the waveguide 7 and the respective individual sensor site 5.

According to a further embodiment, the sample plate comprises at least two fluid channels 8 and respective waveguides 7. The number of fluid channels 8 can be for example 2, 3, 4 or 5. Of course, it is possible to use even greater number of fluid channels 8.

According to a further embodiment, the waveguide 7 is an optical waveguide and the sample plate 1 is configured for optical excitation signals.

According to an embodiment, there is also provided a method of analyzing a sample, the method comprises:
  bringing the sample in contact with at least one sensor site 5 on a substrate 2;
  exciting the sensor site 5 in contact with the sample by means of an evanescent field generated by an excitation signal propagating in a waveguide 7 in order to obtain an emitted signal;

selectively collecting the emitted signal by means of at least one optical element 6 and utilizing a supercritical angle fluorescence method; and detecting the selectively collected emitted signals by a detector.

According to another embodiment, the method comprises bringing the sample in contact with the at least one sensor site 5 through a fluid channel 8 on the substrate 2.

According to a further embodiment, the method comprises bringing the sample into the fluid channel 8 by causing the sample to be absorbed by resilient absorbent material 10 on a sample collection area 9 connected to the fluid channel 8; and compressing the resilient absorbent material 10 so that at least a portion of the sample is squeezed into the fluid channel 8.

More specific embodiments, combining many of the advantageous general embodiments mentioned above, are described below. Basic idea underlining these embodiments is to fulfil the following needs by solving the associated technical problems: In many different detection and diagnostic applications there is a continuous need for a) more sensitive, b) faster and c) smaller, but still d) cost-effective e) sensor arrays that f) do not require complex sample treatment/rinsing and g) allow real-time measurements. The specific embodiments discussed below provide solutions to all these needs.

A novel surface-sensitive fluorescence (SSF) measurement system utilising simultaneously both the total internal reflection (TIR) excitation and supercritical angle fluorescence (SAF) detection principles has already been developed and its benefits—providing answers to needs a), b), f) and g) stated above—demonstrated at VTT [1, 2]. The present embodiments relate to the transfer of the key parts of the measurement system to such an integrated format that also the rest of the needs listed above, i.e. needs c), d) and e) are met.

This embodiment comprises a slide, preferably made of plastic or other cost-effective mass producible material providing sufficient optical properties and transparency for the selected excitation and emission wavelengths, as well as sufficient chemical properties for the target-specific functionalization of assay interfaces. The slide can be a sample plate 1 of FIG. 1, for instance, whereby the material refers to the material of the substrate 2. The idea is to integrate both the fluidic elements/channels, such as fluid channels 8, for the sample collection/transport and the waveguides 7 and other optical elements 6 (e.g. diffractive lenses or other light guiding structures) in/on a single slide or chip. Integrated waveguides are applied to transmit light to the targets (to the points of measurement), while the excitation of the fluorescence labels is performed by the evanescence field of the total internal reflections extending into the sample only to the very vicinity of the slide-sample interface where the target molecules are attached. The fluorescence emitted into the half-space of the slide (to the medium of the higher refractive index) at or above the critical angle of the total internal reflection—i.e. the fluorescence stemming only from the very vicinity of the interface—is collected by applying diffractive optical elements (lenses) or other integrated structures facilitating the collection of light emitted to the desired angles.

In a typical prior diagnostic assay the target molecules (analytes) as well as the fluorescent labelled molecules—used to identify the targets and generate the optical signal—are immobilised on the bottom of a sample vessel (e.g. the well of a microtitter plate) via specific molecular interactions. In commercial fluorometers, widely used e.g. in clinical assays, both the excitation and the collection of the fluorescence emission are typically performed from above the sample vessel through the sample liquid. This configuration makes real-time measurements impossible due the fact that the fluorescent-labelled molecules not bound to their targets are also excited and their emission collected—resulting to a high background signal—unless additional rinsing/separation steps are used to remove the unbound labelled molecules before performing the measurement. Therefore, the analyses can take from several hours to days with all the incubation and rinsing steps. Although the utilisation of fluorescence resonance energy transfer (FRET) facilitates real-time measurements also with the conventional fluorometers, so far its use in diagnostic applications has been limited probably due to the difficulties in measuring the low intensities typical for FRET [3]. Another disadvantage of the conventional fluorometer configuration in surface-based assays relates to the light collection efficiency: The highest emission intensity from a fluorescent molecule located at a dielectric interface is generated towards the side of the higher refractive index at/above the critical angle of total internal reflection, i.e. supercritical angle fluorescence (SAF). Thus, a fluorescent label at the interface of the sample solution and the bottom of the well (e.g. plastics) generates most of its emission downwards away from the detector located above [1]. The distribution of the emission depends on the refractive indices of the system and on the distance of the molecule from the interface. SAF decays approximately exponentially with the distance to the interface. Thus, the conventional fluorometers collecting the upward emitted light miss the highest emission intensity of the surface-bound fluorescent molecules. As a further disadvantage of the commercial fluorometers one can mention the relatively sizable instruments with high costs.

The surface-sensitive fluorescence measurement concept mentioned above enables fast real-time measurements with effective background suppression by applying simultaneously both total internal reflection (TIR) excitation and supercritical angle fluorescence (SAF) detection principles. By combining these two techniques the measurements can be made extremely sensitive and selective to surface-bound fluorescence with an excellent signal-to-noise ratio. In the present laboratory setup a parabolic lens is used to convert SAF into parallel rays for efficient light collection [1]. The same lens is also used for realising the TIR excitation. The SAF-based emission collection principle was previously demonstrated by Ruckstuhl et al. [4] and Enderlein at al. [5] for a biosensor and utilized widely e.g. in fluorescence microscopy. We have combined the TIR excitation technique with SAF in a parabolic setup to further enhance the surface sensitivity and selectivity of the measurements [1].

An embodiment integrates the key elements (optics, fluidics and sample collection) into a single slide enabling the above mentioned advantages in a small, cost-effective multianalyte (array) sensor. One such embodiment is shown in FIGS. 1 and 2, which shows an integrated SSF measurement slide (not in scale).

The sample plate of FIG. 1 comprises a sample collection area 9, which can be made of a pad (or a plurality of pads) with a rough surface combined with an absorbent material underneath. The sample collection area 9 can be adapted, for example, for collection of saliva samples directly from the mouth/tongue. The sample collection area 9 can also be adapted to form just a basin for sample loading. The fluid channel 8 (or plurality of fluid channels 8) transports the sample from the sample collection area 9 to the points of measurement at sensor cites 5 functionalised accordingly to provide specific attachment of the analytes (and fluorescent labels) on the surface. The light for excitation is coupled to a waveguide 7 integrated into the slide (a ridge waveguide at the bottom shown in FIGS. 1 and 2). The light propagating in the waveguide 7 by total internal reflections generates an evanescent field into the fluid channel 8 containing the sensor cites 5. Only the fluorescent molecules within the evanescent field (i.e. very close to the interface) are excited to emit fluorescent light. The optical elements 6, which can be formed by diffractive elements or other integrated (e.g. Fresnel lens type) structures facilitating the collection of the light emitted to the desired angles, collect the emitted light with the highest intensity, i.e. at/above the critical angle of total internal reflection. The light emitted at smaller angles is blocked by non-transparent/absorbing films/coatings/blockers on/under the bottom of the waveguide 7 and to the other direction by the appropriate blockers and structures, e.g. reflective surfaces or diffractive elements.

The above-described embodiment combines several advantages previously not achieved in a single device. This is achieved by implementing a novel integrated slide design. The embodiment provides the following advantages:

very high surface sensitivity and selectivity→no need to rinse→simple assays and real-time measurements possible→reliable results can be obtained in 1-2 minutes or less (fast)

facilitates measurements in opaque liquids (e.g. saliva and serum) efficient light collection→cheap detectors and light sources can be used convenient sample loading integrated fluidic channels→applicable on the field, e.g. for road-side testing small-size format→less reagents and sample needed plastic or other low cost material can be used for the integrated chip→low cost According to an embodiment, the cost of the photodiode arrays used can be for example 10-20 €/piece. According to another embodiment, the cost of the laser diode used (<1 mW) can be 5-40 €/piece.

According to an embodiment, low cost sample plates 1 can be produced by polymer injection moulding. Cost can be for example approximately 10 euro cents per chip at high volumes.

According to another embodiment, low cost sample plates 1 can be produced by nanolithography or nanoimprinting. Cost can be for example approximately a few euros per chip.

According to a further embodiment, very low cost sample plates 1 can be produced by hot-embossing. Cost can be for example approximately a few euro cents per chip.

There are also various alternative embodiments, some of which are discussed below by reference to WO 2011/141530 A2. Therefore, the content of WO 2011/141530 A2 is incorporated herein by reference.

An embodiment of the present invention comprises the substrate of WO 2011/141530 A2 provided with a waveguide for bringing the excitation light to the at least one sensor site.

In another embodiment, the waveguide extends along a surface of the substrate of WO 2011/141530 A2.

In a further embodiment, a sensor comprises a substrate having a first surface and a second surface comprising an optical element. The first surface has at least one sensor site provided thereon and the substrate is configured such that on excitation of a sample provided at the sensor site, luminescence originating from the sensor site propagates into the substrate. The substrate further comprises a waveguide on the second surface to be used in transmitting the excitation signal to the at least one sensor site. For this purpose, the at least one sensor site is located above the waveguide in the substrate. The optical element of the second surface of the substrate is configured to selectively transmit the luminescence propagating within the substrate at angles greater than the critical angle out of the substrate where it is detected by a detector provided below the substrate.

In an embodiment, the optical element is located, in a vertical direction, between the at least one sensor site and the waveguide.

In an embodiment, the optical element is configured to at least partially surround a portion of the material of the substrate between the waveguide and the at least one sensor site.

In an embodiment, the optical element is configured to at least partially surround at least one sensor site.

In an embodiment, the optical element is located at least partially on the level of the waveguide.

In an embodiment, the substrate comprises a plurality of sensor sites each located above the waveguide at different longitudinal positions along the waveguide, and an optical element between each of the sensor sites and the waveguide in the vertical direction.

In a further embodiment, the first surface of the substrate forms a recess that defines a fluid channel within the substrate. In this embodiment, the sensor sites are located at a bottom of the recess so that a fluid sample can be transported to the sensor sites along the fluid channel.

In an embodiment, the fluid channel and the waveguide are both longitudinal and co-directional.

According to an embodiment, a novel integrated slide design is implemented, wherein both total internal reflection (TIR) excitation and supercritical angle fluorescence (SAF) detection are applied simultaneously in a small, cost-effective multianalyte (array) sensor together with the fluidic elements/channels for the sample collection and transport.

Many of the above-discussed embodiments make it possible to combine several advantages (see the listed needs above) previously not achieved in any single device.

According to an embodiment, an integrated sample plate 1 is provided to meet all the listed needs from a) to g).

The above description is only to exemplify the invention and is not intended to limit the scope of protection offered by the claims. The claims are also intended to cover the equivalents thereof and not to be construed literally.

LIST OF REFERENCES CITED IN THE DESCRIPTION

[1] H. Välimäki and K. Tappura, A novel platform for highly surface-sensitive fluorescent measurements applying simultaneous total internal reflection excitation and super critical angle detection, Chemical Physics Letters 473 (2009) 358-362.

[2] H. Välimäki, T. Pulli and K. Tappura, Applying total internal reflection excitation and super critical angle fluorescence detection to a morphine assay, Journal of Fluorescence 20 (2010) 1003-1008.

[3] Lakowicz, J. R., Principles of Fluorescence Spectroscopy, $2^{nd}$ Ed. Kluwer, N.Y. 1999.

[4] Ruckstuhl T., Rankl M., Seeger S., Highly sensitive biosensing using a supercritical angle fluorescence (SAF) instrument. Biosens. Bioelectron. 18 (2003) 1193-1199.

[5] Enderlein J., Ruckstuhl T., Seeger S., Highly efficient optical detection of surface-generated fluorescence. Appl. Opt. 38 (1999) 724-732.

[6] MacCraigth B., Ruckstuhl T., Polymer biochip for detecting fluorescence. U.S. Pat. No. 7,750,316 B2. Date of patent: Jul. 6, 2010.

[7] Shanks I. A., Smith A. M., Photometric instruments, their use in methods of optical analysis, and ancillary devices therefor. U.S. Pat. No. 4,810,658. Date of patent: Mar. 7, 1989

LIST OF REFERENCE NUMBERS 1 sample plate
2 substrate
3 first surface
4 second surface
5 sensor site
6 optical element
7 waveguide
8 fluid channel
9 sample collection area
10 resilient absorbent material

The invention claimed is:

1. A sample plate comprising:
    a substrate;
    at least one sensor site on a first surface of the substrate;
    a waveguide provided on a second surface of the substrate configured to guide an excitation signal to generate an evanescent field for exciting the at least one sensor site; and
    at least one optical element provided on the second surface configure to selectively collect signals emitted in response to said excitation of the at least one sensor site wherein the at least one sensor site, the waveguide and the at least one optical element are integrated in the sample plate.

2. The sample plate of claim 1, wherein the sample plate is configured such that the excitation signal propagating in the waveguide by total internal reflections generates an evanescent field interacting with the at least one sensor site.

3. The sample plate of claim 1, wherein the sample plate is configured such that, on excitation of a sample provided at the at least one sensor site, fluorescent light originating from the sensor site propagates into the substrate and the at least one optical element selectively transmits the fluorescent light within the substrate at angles greater than the critical angle and out of the substrate for detection by a detector.

4. The sample plate according to claim 1, further comprising a fluid channel defined by a recess in the first surface, the at least one sensor site being located within the fluid channel.

5. The sample plate of claim 4, further comprising a sample collection area connected to the fluid channel, the sample plate being configured to receive a fluid sample at the sample collection area and transport at least a portion of the fluid sample via the fluid channel to the at least one sensor site.

6. The sample plate of claim 5, further comprising resilient absorbent material at the sample collection area, the resilient absorbent material configured to absorb the fluid sample and release at least a portion of the absorbed the fluid sample to the fluid channel when the resilient absorbent material is pressed.

7. The sample plate according to claim 4, wherein:
    the waveguide is co-directional with the fluid channel; and
    the at least one sensor site comprises a plurality of sensor sites located along the fluid channel.

8. The sample plate according to claim 4, wherein the at least one optical element comprises an individual optical element for each individual sensor site.

9. The sample plate according to claim 4, comprising at least two fluid channels and respective waveguides.

10. The sample plate according to claim 1, wherein the waveguide is an optical waveguide and the sample plate is configured for optical excitation signals.

* * * * *